United States Patent
Gulliver et al.

(10) Patent No.: US 10,821,253 B2
(45) Date of Patent: Nov. 3, 2020

(54) ADAPTABLE PATIENT INTERFACE WITH CREEP ZONES

(71) Applicant: Fisher & Paykel Healthcare Limited, Auckland (NZ)

(72) Inventors: Laurence Gulliver, Auckland (NZ); Jason Allan Klenner, Auckland (NZ); Sooji Hope Clarkson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 730 days.

(21) Appl. No.: 15/508,837

(22) PCT Filed: Sep. 24, 2015

(86) PCT No.: PCT/IB2015/057348
§ 371 (c)(1),
(2) Date: Mar. 3, 2017

(87) PCT Pub. No.: WO2016/046776
PCT Pub. Date: Mar. 31, 2016

(65) Prior Publication Data
US 2019/0083733 A1 Mar. 21, 2019

Related U.S. Application Data

(60) Provisional application No. 62/166,539, filed on May 26, 2015, provisional application No. 62/055,882, filed on Sep. 26, 2014.

(51) Int. Cl.
*A61M 16/06* (2006.01)
(52) U.S. Cl.
CPC .... *A61M 16/0666* (2013.01); *A61M 16/0683* (2013.01); *A61M 2207/10* (2013.01)

(58) Field of Classification Search
CPC .......... A61M 16/0666; A61M 16/0672; A61M 16/0677; A61M 16/0683
See application file for complete search history.

(56) References Cited

U.S. PATENT DOCUMENTS

| | | | |
|---|---|---|---|
| 6,684,882 B1 | 2/2004 | Morine | |
| 7,735,490 B2 * | 6/2010 | Rinaldi | A61M 16/0666 128/202.27 |
| 9,095,673 B2 * | 8/2015 | Barlow | A61M 16/06 |
| 2005/0066976 A1 * | 3/2005 | Wondka | A61M 16/06 128/207.18 |
| 2012/0145157 A1 | 6/2012 | Lang et al. | |
| 2014/0202465 A1 | 7/2014 | Kooij et al. | |
| 2015/0209541 A1 * | 7/2015 | Harwood | A61M 16/0666 128/205.25 |

OTHER PUBLICATIONS

International Search Report; PCT/IB2015/057348; dated Jan. 19, 2016; 4 pages.

* cited by examiner

*Primary Examiner* — Timothy A Stanis
*Assistant Examiner* — Charles M Vivian
(74) *Attorney, Agent, or Firm* — Knobbe Martens Olson and Bear, LLP

(57) ABSTRACT

A patient interface used in a respiratory care system. The patient interface having an un-deflected configuration, a deflected configuration, and a formed configuration. The patient interface is adapted to elastically deflect, under the application of force, from the un-deflected configuration to the deflected configuration, and permanently deform when in the deflected configuration by mechanical creep deformation to the formed configuration.

20 Claims, 11 Drawing Sheets

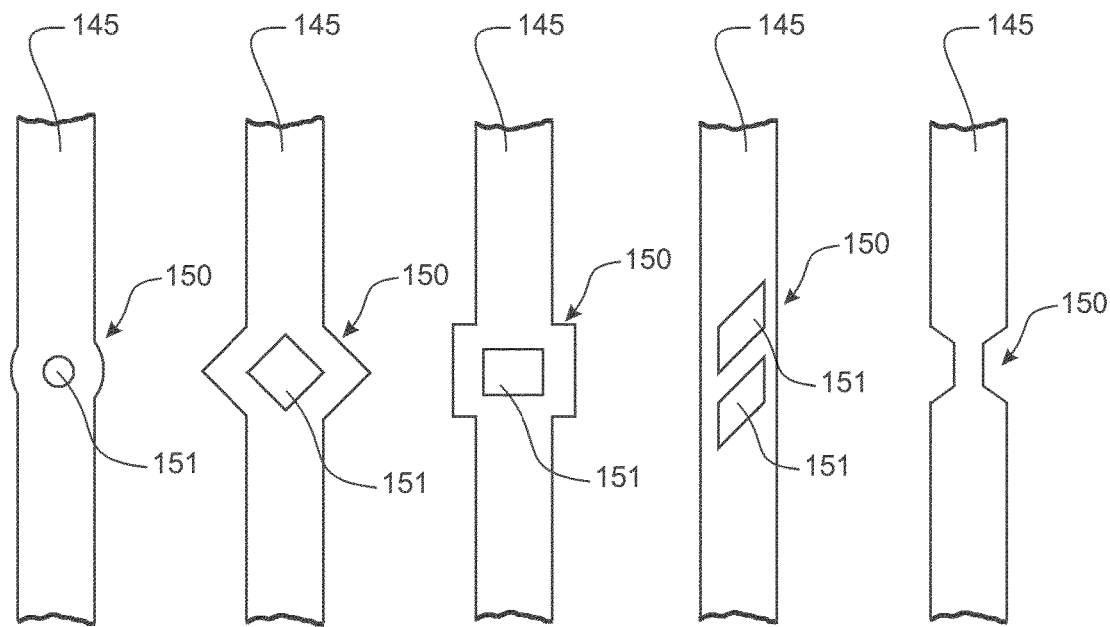
FIGURE 13A　　FIGURE 13C　　FIGURE 13E
　　FIGURE 13B　　FIGURE 13D
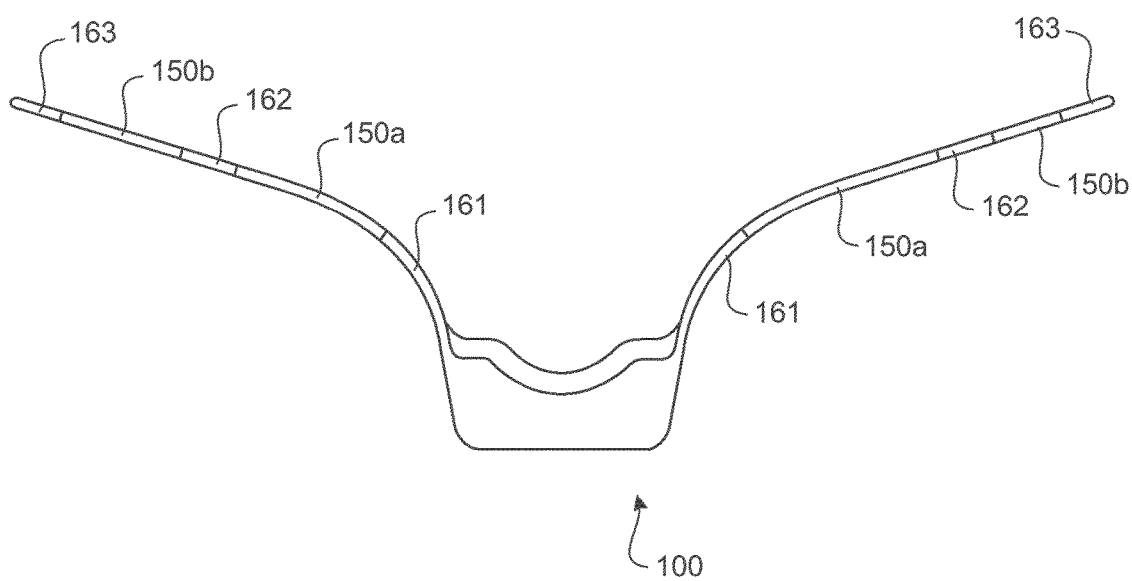
FIGURE 14

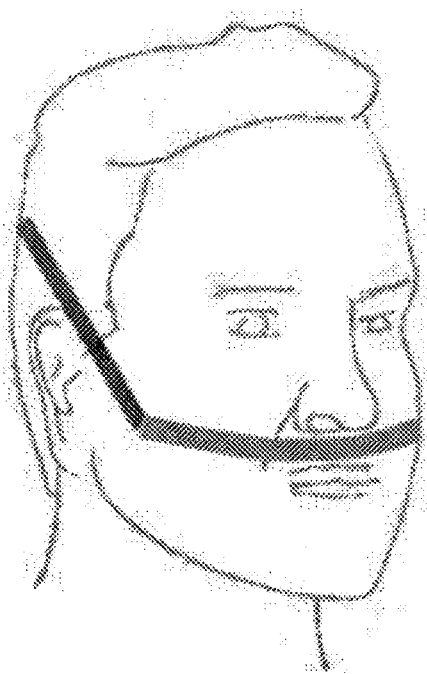
FIGURE 18A
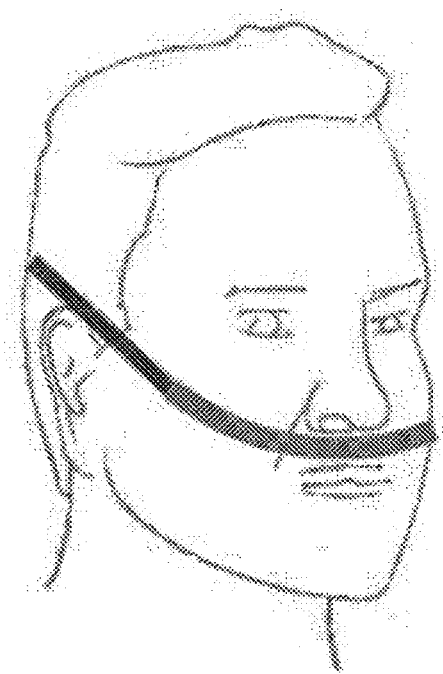
FIGURE 18B
FIGURE 19
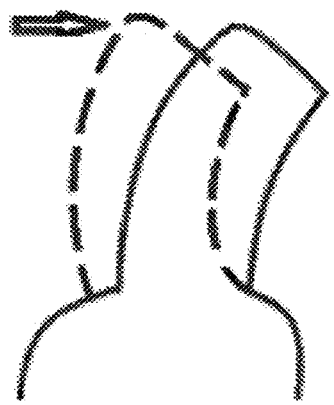

ADAPTABLE PATIENT INTERFACE WITH CREEP ZONES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The invention relates to a patient interface, such as a nasal cannula, for the delivery of gases to a patient.

BACKGROUND OF THE INVENTION

For providing a flow of respiratory gases to a patient or user it is important to provide a patient interface that is comfortable, easy to wear and one that retains its operational position (therapy delivery position) on the user's face during use.

Providing for alternative patient interface and headgear systems allows for users to choose the style or type of equipment to use. Such selection may be made upon comfort, or better suited retention of the patient interface upon a user for improved respiratory therapy delivery, or both of these.

To assist in ensuring the patient interface is comfortable, easy to wear and retains its operational position on the user's face during use, preferably the force required to fit the patient interface to the contours of the user's face is of a low magnitude. A high force creates an undesirable amount of pressure on the user's face that can quickly result in pain or discomfort during use. The amount of force required to fit a user interface to a user's face may be kept to a minimum by providing an interface formed solely from a resilient material such as silicone or other thermoplastic elastomer. However, such an interface may lack structural integrity, resulting in movement of the interface on the user's face or excessive elastic deformation of the interface in use. Ideally a customized interface would be provided for every individual user. A customized interface can be designed to match a particular user's facial features and be of sufficient structural integrity so that the force for maintaining the interface in the correct position on the user's face is reduced. However, it is not practical to provide a specially customized interface for every user, or even many interfaces to match many different users.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide an improved patient interface or to at least provide the public with a useful choice.

SUMMARY OF THE INVENTION

In one aspect, the present invention broadly consists in a patient interface comprising:

a manifold adapted to receive a flow of gases, one or two gas outlets, such as nasal prongs extending from the manifold, and a side arm extending from each side of the manifold, each side arm adapted to conform to a profile of a user's face by mechanical creep deformation during use.

In another aspect, the present invention broadly consists in a patient interface comprising:

a manifold adapted to receive a flow of gases, one or two gas outlets, such as nasal prongs extending from the manifold, and a side arm extending from each side of the manifold, in use, headgear attached to the side arms for securing the patient interface to a user's face, force in the headgear causing the side arms to elastically deflect and conform to a profile of the user's face, and the side arms adapted to deform by mechanical creep deformation in use so that a force required to elastically deflect the side arms to conform to the profile of the user's face diminishes over time.

In another aspect, the present invention broadly consists in a patient interface comprising:

a manifold adapted to receive a flow of gases, one or two gas outlets, such as nasal prongs extending from the manifold, and a side arm extending from each side of the manifold, each side arm adapted to:

elastically deflect, under a force applied by headgear, from an un-deflected configuration at least partly displaced from the user's face to a deflected configuration in which the side arms conform with a profile of the user's face, and permanently deform, under the force applied by headgear, by mechanical creep deformation in use to reduce the force required to maintain the side arms in the elastically deflected configuration over time.

In another aspect, the present invention broadly consists in a patient interface adapted to elastically deflect, under the application of a force, from an un-deflected configuration to a deflected configuration, and permanently deform when in the deflected configuration by mechanical creep deformation to a formed configuration.

In some embodiments, the interface comprises a manifold adapted to receive a flow of gases, one or two gas outlets, such as nasal prongs extending from the manifold, and a side arm extending from each side of the manifold, each side arm adapted to:

elastically deflect, under the application of the force, from the un-deflected configuration to the deflected configuration in which the side arms conform with a profile of the user's face, and permanently deform, under the applied force, by mechanical creep deformation to the formed configuration in which the side arms conform with the profile of the user's face.

In some embodiments, the interface comprises a manifold adapted to receive a flow of gases, one or two nasal prongs extending from the manifold, and a side arm extending from each side of the manifold, and wherein each nasal prong is adapted to:

elastically deflect, under the application of the force, from the un-deflected configuration to the deflected configuration in which the nasal prongs conform with a profile of the user's face, and permanently deform, under the applied force, by mechanical creep deformation to the formed configuration in which the nasal prongs conform with the profile of the user's face.

In some embodiments, the interface is adapted to:

elastically deflect, under a force applied by headgear in use, from the un-deflected configuration to the deflected configuration, and permanently deform by mechanical creep deformation, under the force applied by headgear in use, to the formed configuration.

In some embodiments, in the formed configuration the interface conforms with the profile of the user's face without application of a force or under a force that is reduced compared to the force applied to elastically deflect the interface from the un-deflected configuration to the deflected configuration.

In some embodiments, the interface comprises one or more creep zones in which mechanical creep deformation is confined or predominant in the interface.

In some embodiments, the creep zone or zones are located in areas that are difficult to fit to a range of user's faces due to large variation between different users.

In some embodiments, the creep zone is formed from a material that is different to the material of other parts of the interface.

In some embodiments, the creep zone is formed a material forming process in the creep zone that is different to a material forming process in other areas of the interface.

In some embodiments, the creep zone is formed after the interface has been moulded by a treatment process.

In some embodiments, the creep zone has a reduced cross section compared to areas of the interface adjacent to the creep zone.

In some embodiments, the creep zone comprises a thinner or narrower section in the interface, and/or a section with a hole or cut-out.

In some embodiments, the creep zone comprises more than one cut out.

In some embodiments, the interface comprises a manifold adapted to receive a flow of gases, one or two gas outlets, such as nasal prongs extending from the manifold, and a side arm extending from each side of the manifold, and wherein each arm comprises one or more said creep zones and one or more dimensionally stable zones.

In some embodiments, each side arm has a creep zone at an intermediate position along the arm, in between two dimensionally stable zones.

In some embodiments, each side arm has a dimensionally stable portion at an inner end of the arm.

In some embodiments, the side arms each comprise at least two said creep zones spaced apart by a dimensionally stable zone.

In some embodiments, each side arm comprises a first dimensionally stable zone at an inner end of the arm and a second dimensionally stable zone partway along the arm, a first creep zone in between the first and second dimensionally stable zones, and a second creep zone outside the second dimensionally stable zone towards or at an outer end of the arm.

In some embodiments, each side arm comprises a dimensionally stable zone at each end of the arm, a third dimensionally stable zone part way along the arm, and two creep zones, each creep zone located between an end of the arm and the third dimensionally stable zone.

In some embodiments, a said dimensionally stable zone comprises a detail for mating with another part.

In some embodiments, the detail is a clip or buckle.

In some embodiments, the manifold is formed in or as a dimensionally stable zone.

In some embodiments, a said creep zone is located in the side arm to correspond with the lower outer maxilla zone, the upper outer maxilla zone, the zygomatic arch, the maxilla recess, or the central maxilla.

In some embodiments, the interface deforms by mechanical creep deformation in areas of high skin contact pressure.

In some embodiments, the interface is adapted to promote mechanical creep deformation by actively heating the interface.

In some embodiments, the interface comprises a heater element such as a heater wire to raise the temperature of the interface to promote mechanical creep deformation.

In some embodiments, the interface comprises a conduit aligned with a deformable portion of the interface so that a flow of heated respiratory gases to be delivered to the patient's airway raise the temperature of the deformable portion to promote mechanical creep deformation.

In some embodiments, the interface comprises a heat pack that dissipates heat by chemical reaction that is user-activated.

In some embodiments, the interface is adapted to deform by mechanical creep deformation at a temperature in the range of about 20° C. to about 150° C., or about 30° C. to about 140° C., or about 40° C. to about 130° C., or about 50° C. to about 120° C.

In some embodiments, stress in the interface causes the interface to permanently deform by mechanical creep deformation over time remains below the yield stress of the material of the side arms.

In some embodiments, each side arm is shaped so that in an un-deflected configuration and with the manifold positioned at or adjacent a user's upper lip for use, an intermediate section of each side arm contacts the user's face.

In some embodiments, each side arm is outwardly curved so that in the un-deflected configuration and with the manifold positioned at or adjacent a user's upper lip for use, the intermediate section of each side arm contacts the user's face.

In some embodiments, in the un-deflected configuration and with the manifold positioned at or adjacent a user's upper lip for use, the intermediate section of the side arm contacts the user's face in one or more of the lower outer maxilla zone, the upper outer maxilla zone, the zygomatic arch, the maxilla recess, and the central maxilla.

In some embodiments, in the un-deflected configuration and with the manifold positioned at or adjacent a user's upper lip for use, the intermediate section of the side arm contacts the user's face in any one or more of the lower outer maxilla, the zygomatic arch and the maxilla recess.

In some embodiments, a force applied to the side arms by headgear in use bends each side arm at the intermediate section in contact with the user's face to, in a deflected configuration, conform to the profile of the user's face.

In some embodiments, a contact force between the manifold and the user's upper lip region is at least reduced when the side arms are defected from the un-deflected configuration to the deflected configuration.

In some embodiments, the side arms permanently deform by mechanical creep deformation over time, under a force applied by headgear in use, to maintain a formed configuration, in the formed configuration the side arms approximately conforming to the profile of the user's face.

In some embodiments, the side arms permanently deform by mechanical creep deformation, under a force applied by headgear in use, over time so that mechanical stress in the side arms during use reduces over time.

In some embodiments, the side arms permanently deform by mechanical creep deformation laterally, vertically, and/or torsionally to conform to the user's face in a deflected or formed configuration.

In some embodiments, the interface comprises a frame and a resilient material at least partly covering the frame, wherein the frame is adapted to deform by mechanical creep deformation to conform to a profile of a user's face.

In some embodiments, the frame comprises side members forming side arms of the interface, the side members of the frame adapted to deform by mechanical creep deformation so that each side arm conforms to a profile of a user's face In some embodiments, each side arm comprises a said side member of the frame and the resilient material covering the side member of the frame.

In some embodiments, the frame extends continuously along each side arm from one side of the patient interface to the other.

In some embodiments, the side members are formed from a material and are of a suitable geometry so that the side arms are adapted to conform to a profile of a user's face by mechanical creep deformation during use.

In some embodiments, side members are formed from a material and are of a suitable geometry such that a combination of one or more of:

i) the temperature reached by the side members during use when fitted to a user's face, and ii) a force applied to the side members by headgear during use when fitted to the user's face, and iii) a period of time the patient interface is fitted to the user's face, provides for an effective amount of permanent deformation by mechanical creep deformation to occur in the side members for an anatomical fitment of the patient interface to the profile of the user's face.

In some embodiments, the resilient material is one of silicone, thermoplastic elastomer, thermoplastic polyurethane.

In some embodiments, the frame comprises a cutout portion facing the user's upper lip in use, the resilient material forming a wall of the manifold at the cut out portion to provide a resilient pillow for contact with the user's upper lip.

In some embodiments, the frame is formed from any one or more of polycarbonate, low density polyethylene, high density polyethylene, polypropylene, low density polypropylene, high density polypropylene, poly-vinyl chloride and ethylene-vinyl acetate.

In some embodiments, the side arms are formed from a material and are of a suitable geometry so that the side arms are adapted to conform to a profile of a user's face by mechanical creep deformation during use.

In some embodiments, side arms are formed from a material and are of a suitable geometry such that a combination of one or more of:

i) the temperature reached by the side arms during use when fitted to a user's face, and ii) a force applied to the side arms by headgear during use when fitted to the user's face, and iii) a period of time the patient interface is fitted to the user's face, provides for an effective amount of permanent deformation by mechanical creep deformation to occur in the side arms for an anatomical fitment of the patient interface to a profile of the user's face.

In some embodiments, the interface is formed from any one or more of polycarbonate, low density polyethylene, high density polyethylene, polypropylene, low density polypropylene, high density polypropylene poly-vinyl chloride and ethylene-vinyl acetate.

In some embodiments, the interface permanently deforms by mechanical creep deformation over a time period of less than 2 weeks or 1 week, or 6 days, or 5 days, or 4 days, or 3 days, or 2 days, or 1 day, or 12 hours, or 2 hours to reach a formed configuration to approximately conform to a profile of a user's face.

In some embodiments, the interface permanently deforms by mechanical creep deformation at a temperature that the interface reaches during use with the patient interface fitted to a user's face.

In some embodiments, the interface permanently deforms by mechanical creep deformation at a temperature of about 18° C. to 37 ° C., or 28° C. to 37° C., or 18° C. to 35° C., or 18° C. to 30° C., or 30° C. to 35 ° C.

In some embodiments, the interface deforms by mechanical creep deformation at a force of about 0.1N to 5N, or about 0.1N to 1.5N, or about 0.1N to 1.0N, or about 0.2N to 0.5N, or about 0.2N to 0.4N, or about 0.2N to 0.3N, or about 0.3N to 0.5N, or about 0.3N to 0.4N, or about 0.4N to 0.5N, or about 0.1N or about 0.2N, or about 0.3N, or about 0.4N, or about 0.5N.

In some embodiments, the present invention broadly consists in a patient interface as described in any one or more of the above statements, and a brace, the patient interface mounted on the brace to hold the patient interface in the deflected position.

In some embodiments, the patient interface and brace are wrapped in packaging for delivery to a user, or the brace forms packaging for packaging the interface for delivery to the user.

In some embodiments, the brace comprises two complementary parts that fit together to form a cavity for receiving and holding the interface in a deflected configuration.

In some embodiments, the brace comprises an open recess or cavity into which the interface is inserted to hold in the deflected configuration.

In some embodiments, the brace comprises a base and retention details extending from the base to hold the interface in the deflected configuration.

In some embodiments, the brace comprises a set of retention details corresponding to more than one deflected or formed configurations.

In another aspect, the present invention broadly consists in a patient interface and a brace, the brace adapted to hold the patient interface in a deflected position, the interface adapted to permanently deform when in the deflection configuration by mechanical creep deformation to a formed configuration to conform with the profile of a user's face.

In some embodiments, the patient interface and brace are wrapped in packaging for delivery to a user.

In some embodiments, the brace forms part of a packing for packaging the patient interface.

In some embodiments, the brace comprises two complementary parts that fit together to form a cavity for receiving and holding the interface in a deflected configuration.

In some embodiments, the brace comprises an open recess or cavity into which the interface is inserted to hold in the deflected configuration.

In some embodiments, the brace comprises a base and retention details extending from the base to hold the interface in the deflected configuration.

In some embodiments, the brace comprises a set of retention details corresponding to a number of different deflected or formed configurations.

In some embodiments, the interface comprises a manifold adapted to receive a flow of gases, one or two gas outlets, such as nasal prongs extending from the manifold, and a side arm extending from each side of the manifold, and the brace adapted to apply a force to the side arms by holding the side arms in the deflected configuration, each side arm adapted to permanently deform under the applied force by mechanical creep deformation to the formed configuration.

In another aspect, the present invention broadly consists in a method for forming a patient interface comprising the steps:

moulding the interface in a moulding process, applying a force to the interface to elastically deflect the interface from a moulded form or un-deflected configuration to a deflected configuration, and permanently deforming the interface when in the deflected configuration by mechanical creep deformation to a formed configuration.

In some embodiments, the interface comprises a manifold adapted to receive a flow of gases, one or two gas outlets, such as nasal prongs extending from the manifold, and a side arm extending from each side of the manifold, and the method comprises:

applying a force to elastically deflect the side arms from the un-deflected configuration to the deflected configuration in which the side arms conform with a profile of the user's face, and permanently deforming the side arms when in the deflected configuration by mechanical creep deformation in which the side arms conform with the profile of the user's face.

In some embodiments, the method comprises:

applying the force to the interface by headgear during use to elastically deflect the interface from the un-deflected configuration to the deflected configuration, and permanently deforming the interface by mechanical creep deformation during use to the formed configuration.

In some embodiments, the method comprises:

applying the force to the interface by fitting the interface in a brace to hold the interface in the deflected configuration, and permanently deforming the interface by mechanical creep deformation while the interface is held by the brace.

In some embodiments, the method comprises packaging the interface and brace together in packaging for delivery to a user.

In some embodiments, the method comprises packaging the interface in the brace for delivery to a user.

In some embodiments, the brace provides more than one deflected or formed configurations, and the method comprises fitting the interface in the brace in one of the deflected or formed configurations.

In some embodiments, the interface is held in the brace to allow for the interface to permanently deform by mechanical creep deformation prior to delivery to a user.

In some embodiments, the method comprises heating the interface to promote or accelerate mechanical creep deformation "Plastic deformation"—non-reversible permanent deformation caused by stressing a material above the yield stress.

"Elastic deflection" or "elastic deformation"—reversible deflection or deformation, the material returns substantially to an initial non-deflected or non-deformed state or shape. Material is not stressed above the yield stress.

"Mechanical creep deformation"—non-reversible permanent deformation caused by stressing a material below the yield stress for an extended period of time.

In this specification and claims, where a patient interface is deformed or formed (elastically or plastically or both) to conform to a profile of a user's face, the statement "conform to a profile of a user's face" is intended to mean that in the deflected or deformed or formed configuration the interface more closely matches the contours of the user's face compared to when in an un-deflected or un-deformed or un-formed configuration.

The terms "upward", "across", and "rearward" as used in this specification in relation to an interface mean (unless the context indicates otherwise) approximately vertical, transversely horizontal, and front to back horizontal through or in relation to the interface when worn by a user standing upright.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the following drawings.

FIGS. 13A to 13E illustrate creep zone geometries for a side arm of an interface.

FIG. 14 illustrates a nasal cannula from below or above (nasal prongs not shown) with more than one creep zone formed in each side arm of the cannula.

FIGS. 18A and 18B illustrate an interface being worn by a user before and after mechanical creep deformation.

FIG. 19 illustrates a nasal prong prior to deformation (dashed lines) and after deformation by mechanical creep deformation.

DETAILED DESCRIPTION OF PREFERRED EMBODIMENTS

Preferred forms of a patient interface according to the present invention are described. It will also be appreciated that various aspects of the present invention may be applied to any form of patient interface including, but not limited to indirect nasal masks (which covers the nose), direct nasal masks that include nozzles (or prongs) or pillows that enter or engage the nares of the wearer, oral masks (which cover the mouth), or full face masks (which cover the nose and mouth), and mouthpieces but will be described with reference to a nasal cannula.

Figure 1:
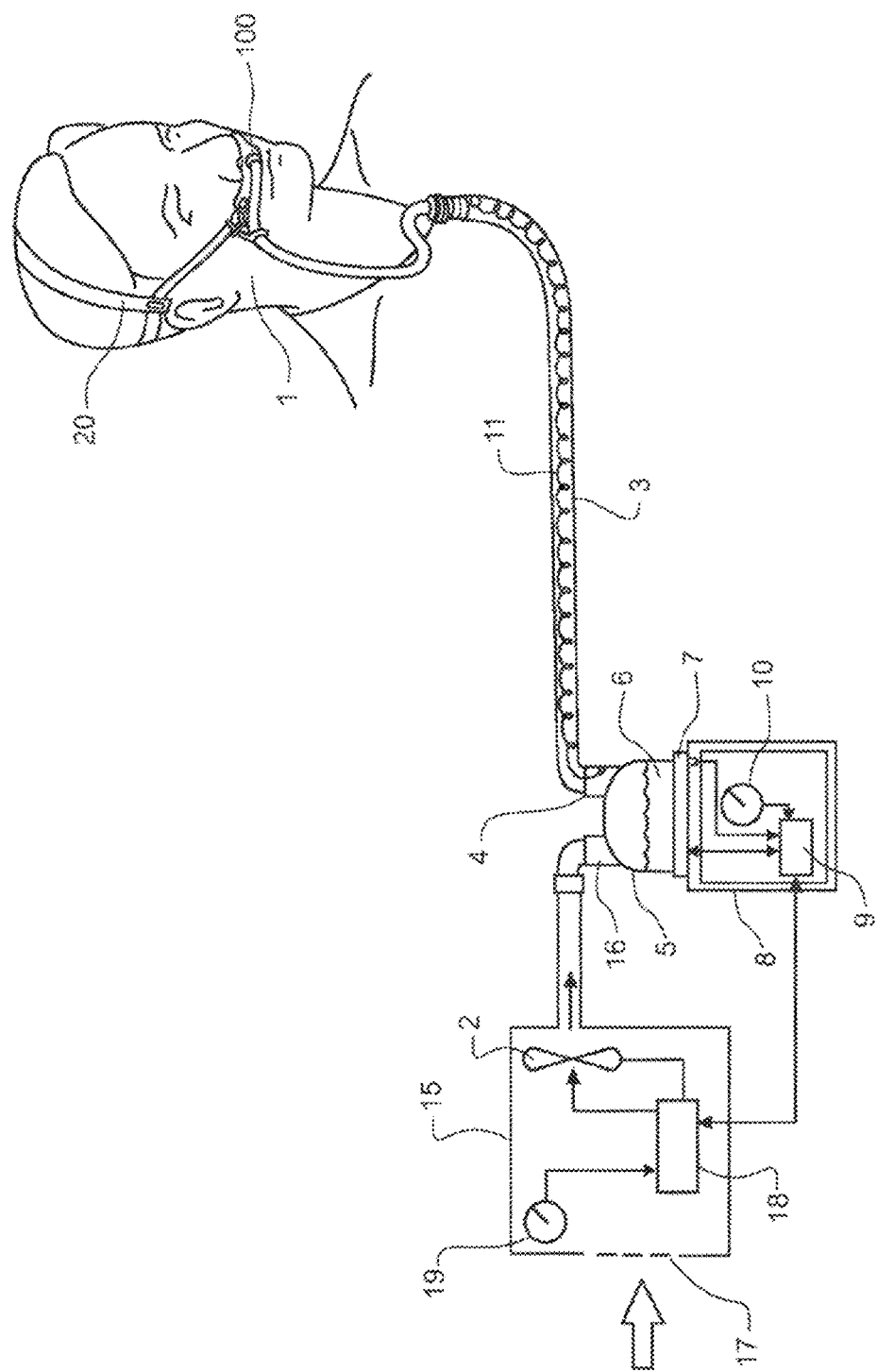
FIG. 1 is a schematic of a respiratory care system.

A patient interface according to the present invention may be used in respiratory care systems, whether high or low flow therapy, or whether as a sealed or non-sealed interface, for example humidified PAP delivery or in-hospital respiratory care systems. FIG. 1 illustrates a typical humidifying respiratory circuit. A patient 1 is receiving humidified and pressurised gases through a nasal cannula assembly 100 connected to a humidified gases transportation pathway or inspiratory conduit 3 that in turn is connected to a humidifier 8 (including humidification chamber 5) that is supplied with gases from a blower 15 or other appropriate gases supply means. Headgear 20 is provided to support and retain the patient interface against the patient's face. The inspiratory conduit 3 is connected to the outlet 4 of a humidification chamber 5 which contains a volume of water 6. Humidification chamber 5 is preferably formed from a plastics material and may have a highly heat conductive base (for example an aluminium base) which is in direct contact with a heater plate 7 of humidifier 8. The humidifier 8 is provided with control means or electronic controller 9 which may comprise a microprocessor based controller executing computer software commands stored in associated memory.

Gases flowing through the inspiratory conduit 3 are passed to the patient by way of the nasal cannula assembly 100.

Controller 9 receives input from sources such as user input means or dial 10 through which a user of the device may, for example, set a predetermined required value (preset value) of humidity or temperature of the gases supplied to patient 1. In response to the user set humidity or temperature value input via dial 10 and other possible inputs such as internal sensors that sense gases flow or temperature, or by parameters calculated in the controller, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. It should be noted that it is possible to obtain the relationship between the humidity of the gases in humidification chamber 5 and the temperature of the heater plate 7. Accordingly, it is possible to utilise the heater plate temperature in an algorithm or a look-up table to determine the humidity of the gases.

The blower 15 may be provided with a variable speed pump or fan 2 which draws air or other gases through the blower inlet 17. The speed of variable speed pump or fan 2 may be controlled by a further control means or electronic controller 18 (or alternatively the function of this controller 18 could be carried out by the other controller 9) in response to inputs from controller 9 and a user set predetermined required value (preset value) of pressure or fan speed via dial 19.

A heating element 11 may be provided within the conduit or tubing 3 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element effectively replaces the energy lost from the gases through conduction and convection during transit through the conduit. Thus the conduit heater element ensures the gases delivered are at an optimal temperature and humidity.

Preferred embodiments of the invention will now be described for the patient interface 100 with reference to FIGS. 2 to 10.

The patient interface 100 of the preferred embodiment is in the form of a nasal cannula 100 that is adapted to couple to an inspiratory conduit and that comprises at least one, but preferably two, nasal prongs 111 and 112 configured to fit within the nares of a patient to deliver a flow of gases to the patient. The cannula comprises a gases flow manifold 120 in fluid communication with the nasal prong or prongs and is configured to be attached to an inspiratory conduit. For example, the manifold may comprise a socket 124 for receiving a connector or end of the conduit. In some embodiments the inspiratory conduit may be integrally formed with the manifold 120, for example over moulded to the manifold.

The nasal prongs 111 and 112 may be curved to extend into the patient's nares in use and to provide a smooth flow path for gases to flow through. The inner surfaces of the prongs 111 and 112 may be contoured to reduce noise. The bases of the prongs 111 and 112 may include curves surfaces to provide for smoother gases flow. This may reduce the noise level during operation.

The nasal prongs 111 and 112 may be consistent in diameter along their lengths but are preferably shaped to fit the contours of the nares. Each prong 111/112 may have an elongated opening 111a/112a at the distal end opposing a base portion 118. In alternative embodiments the nasal prongs 111 and 112 may have a tapered profile of a wider end at the base portion 118 and a narrower end at the openings 111a and 112a, and vice versa.

The patient interface comprises side arms extending from a central part of the patient interface. For example, the cannula comprises side arms 145a, 145b extending from the manifold 120 of the cannula. In use, headgear is attached to the side arms to support the cannula in place on a user's face. For example, a head gear strap is clipped to ends 142 of the side arms.

Figure 2:
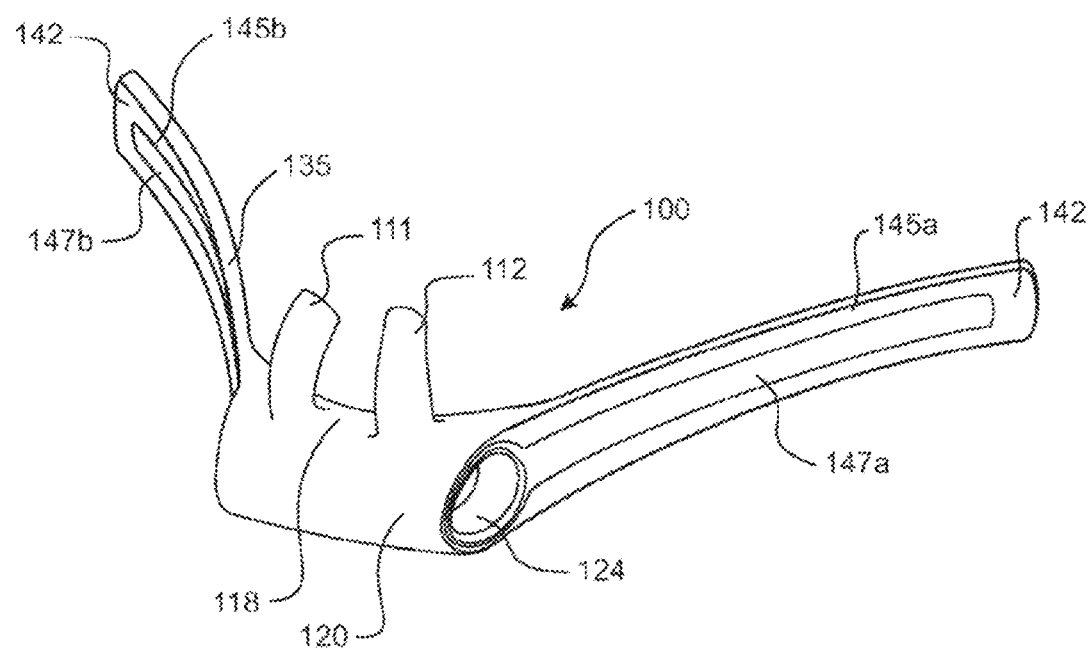
FIG. 2 is a perspective view of a cannula according to some embodiments of the present invention.

In FIG. 2 a cannula according to some embodiments of the present invention is shown in an un-deflected or un-deformed position or state prior to use. In the un-deflected position, at least a portion of the side arms are spaced from a user's face. For example, as shown in plan view in FIG. 8, at least end portions 141 of the side arms are spaced from the user's face or do not conform with contours of the user's face.

Figure 8:
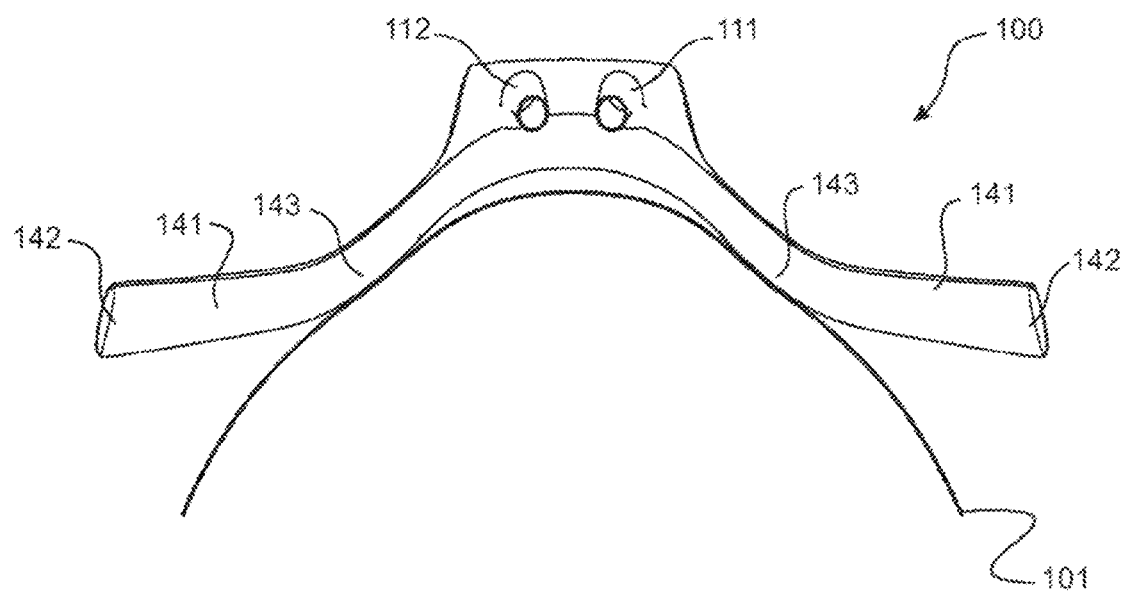
FIG. 8 is a plan view of the cannula of FIG. 2 shown in position against the upper lip region of a user's face.
Figure 9:
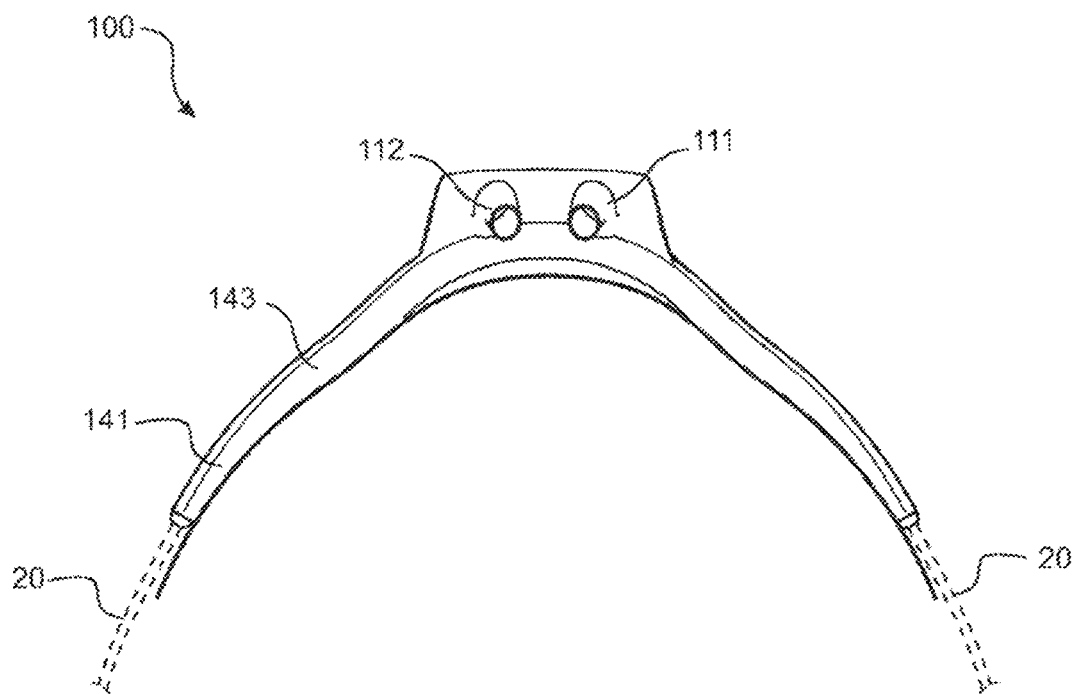
FIG. 9 is a plan view of the cannula of FIG. 2 shown in position against the upper lip region of a user's face and with side arms of the cannula deflected and/or deformed to conform to the profile of the user's face.

In use, head gear deflects or deforms the side arms of the cannula to conform to the profile of the user's face, for example as illustrated in plan view in FIG. 9. Force provided by the headgear pulls the side arms from the un-deflected configuration shown in FIG. 8 to a deflected or deformed configuration shown in FIG. 9. In the deflected/deformed configuration the side arms of the interface conform more closely with a profile 101 of the user's face than in the un-deflected position.

In an interface according to the present invention, each side arm of the interface is adapted to conform to a profile of a user's face by mechanical creep deformation during use. The side arms may be formed from a material and of a suitable geometry to provide for a useful amount of mechanical creep deformation to customise the interface to fit an individual during use.

In use, the headgear initially elastically deflects the interface to conform to the profile of the user's face. Then, during use, the side arms deform by mechanical creep deformation so that a force required to elastically deflect the side arms to the profile of the user's face diminishes over time. Through use, mechanical creep deformation of the interface material results in the interface permanently deforming to more closely match the contours of the user's face. Thus an interface according to the present invention is somewhat customized to each particular user's face during use. In some embodiments the headgear initially elastically deflects and plastically deforms the interface to conform to the profile of the user's face.

In some embodiments, the side arms are adapted to permanently deform by mechanical creep deformation, under the force applied by headgear, to a formed configuration. For example, a formed configuration may preferably provide for a customised fit to a user.

In the formed configuration the side arms approximately fit to a profile of the user's face. In the formed configuration the interface approximately fits the user's face under a reduced force compared to the force required to initially elastically deflect the side arms to fit the user's face. In some embodiments, in the formed configuration the patient interface anatomically fits the user's face.

In some embodiments in the formed configuration the interface approximately fits the profile of the user's face with a minimal or reduced force provided by headgear.

Under a force applied by headgear in use, over time, the side arms deform by way of mechanical creep deformation. As a result, elastic deflection and/or mechanical stress in the side arms during use reduces over time. This causes the force required to keep the side arms in position on the user's face to be reduced compared to when the side arms are initially elastically deflected to fit the user's face.

To fit the user's face the side arms may permanently deform by way of mechanical creep deformation laterally, vertically, and/or torsionally. For example, with reference to FIGS. 8 and 9, the side arms in FIG. 9 have been deflected at least laterally and torsionally to lie against the profile of the user's face. Torsion or twist of the side arms causes the side arms to lie flatter on a user's face which can reduce pressure against the user's face caused by edges of the side arms pressing against the user's face.

The side arms are of a suitable geometry and formed from a suitable material to deform by mechanical creep deformation during use. Prior art patient interfaces typically include relatively rigid materials, for example for manifolds or mask bodies, and soft or resilient materials attached to the relatively rigid materials for contacting the user's face during use. The resilient materials, for example resilient material forming nasal prongs or a face seal, elastically deform during use but do not deform permanently, whereas the relatively rigid materials, for example a material forming a mask body of a patient interface, do not permanently deform during use, and do not elastically deform to approximate a profile of the user's face.

In some embodiments of the present invention, the side arms 145a, 145b comprise a relatively rigid material. For example, in some embodiments, the side arms are formed from polycarbonate, high-density polyethylene, low density polyethylene, polypropylene, poly-vinyl chloride, ethylene-vinyl acetate or any other suitable relatively rigid plastics material. The side arms formed from a relatively rigid material are shaped or are of a particular geometry to initially elastically deflect to conform to a profile of a user's face, and then deform by mechanical creep deformation over time during use. For example the side arms are of a suitable material and cross section to allow the side arms to deform by mechanical creep deformation under force provided by headgear during use to hold the patient interface in place on the users face.

Figure 4:
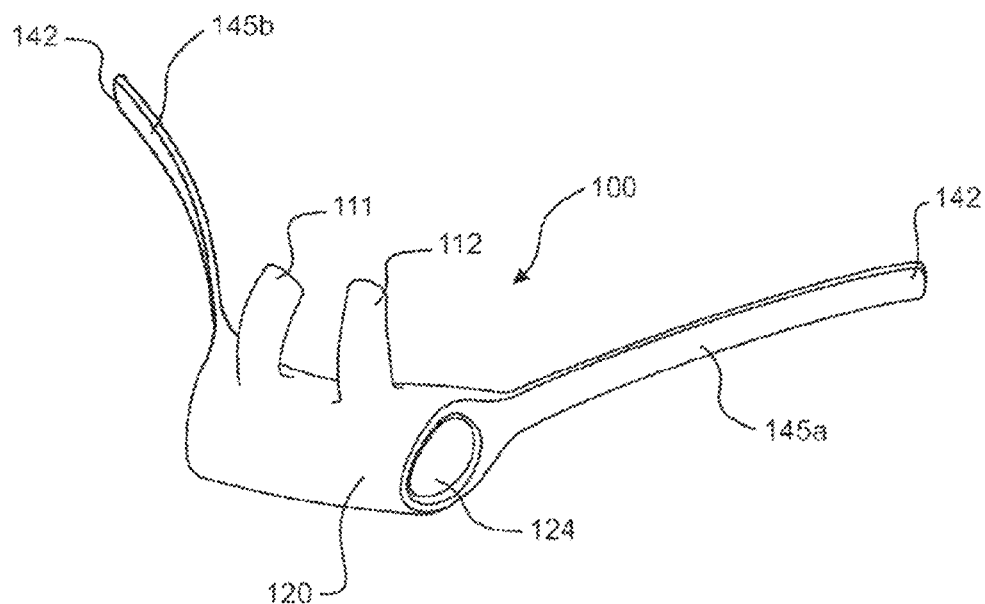
FIG. 4 is a perspective view of an alternative cannula according to some embodiments of the present invention.

In some embodiments the side arms 145a, 145b are integrally formed with the manifold 120 and the nasal prongs 111, 112 as a single unitary member, for example as shown in FIG. 4. Such an embodiment may be less preferred than other embodiments described below as the nasal prongs are formed from the same material as the side arms and may be relatively rigid. Preferably the nasal prongs 111, 112 are formed from a resilient material to interface with the user's nostrils.

Figure 5:
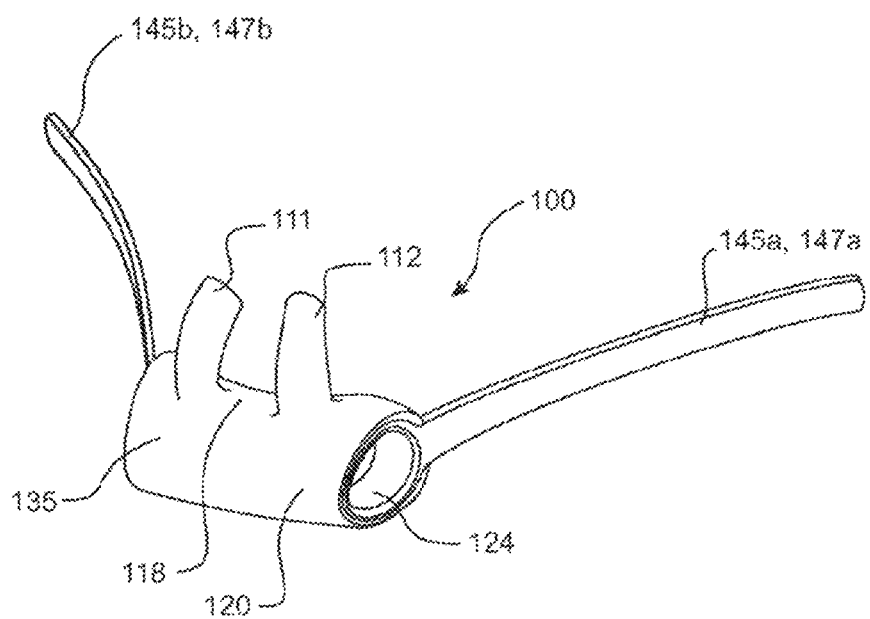
FIG. 5 is a perspective view of another alternative cannula according to some embodiments of the present invention.
Figure 6:
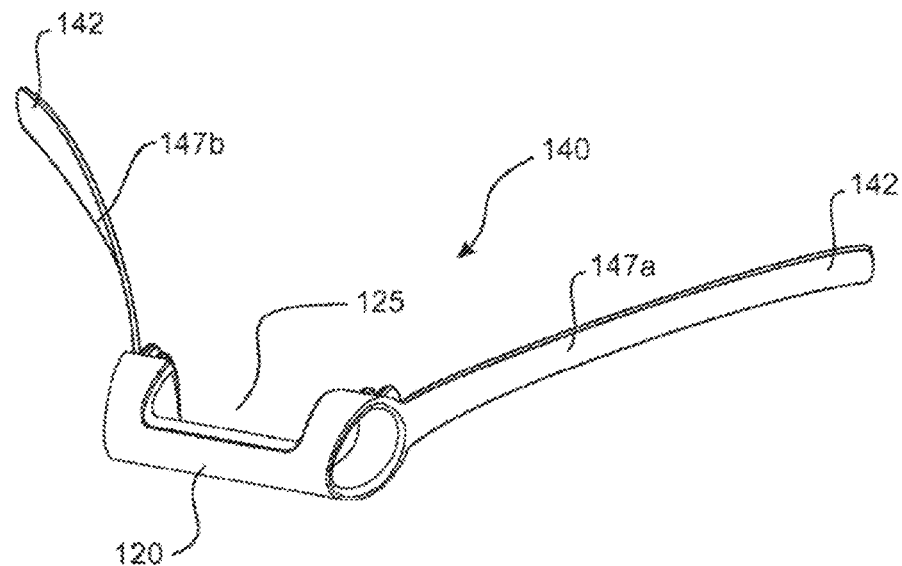
FIG. 6 is a perspective view of a frame of the cannulas of FIG. 2 and FIG. 5.
Figure 7:
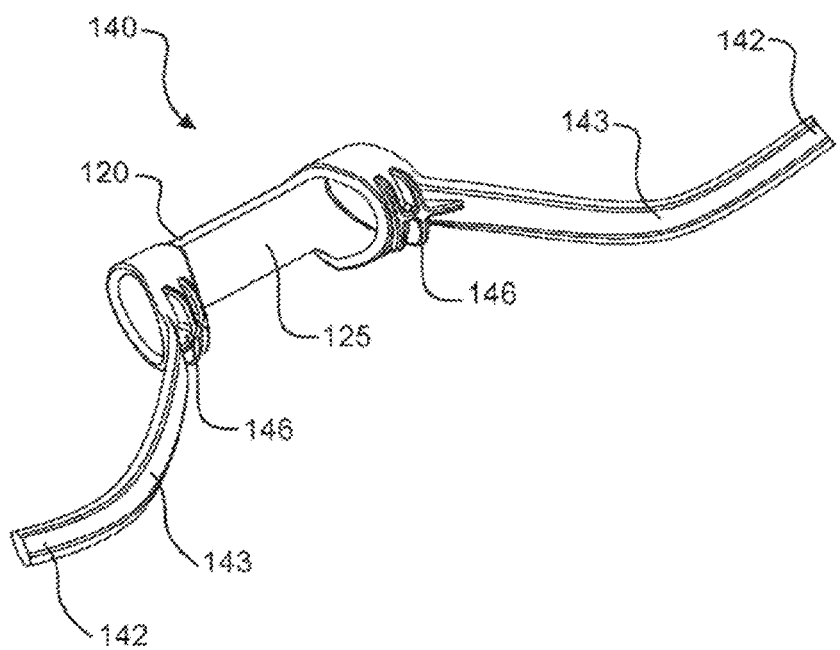
FIG. 7 is a perspective view of the frame of FIG. 6 viewed from an inner side of the frame.

In some embodiments the patient interface comprises a frame. An example frame 140 is illustrated in FIGS. 6 and 7. The frame may be formed from a relatively rigid material. Examples of possible rigid materials are provided above. The frame comprises side members 147a, 147b. In some embodiments the side members of the frame form the side arms 145a, 145b of the cannula, for example, as shown in FIG. 5. In the embodiment of FIG. 5, the manifold of the cannula is over moulded or otherwise covered (either partially or completely) with a soft, flexible or resilient material 135 such as Silicone, thermoplastic elastomer (TPE), and/or thermoplastic polyurethane (TPU) or other material known in the art. The resilient material covers the manifold of the cannula or forms the manifold together with a manifold part of the frame. The resilient material covering or forming the manifold may contact the user's face in use. In the illustrated embodiment, the nasal prongs are integrally formed with the resilient material covering the frame. In some embodiments, the frame comprises the manifold and side arms, and the nasal prongs are over moulded to the manifold of the frame. The frame is relatively rigid compared to the resiliency of the over moulded material forming the nasal prongs.

Figure 3:
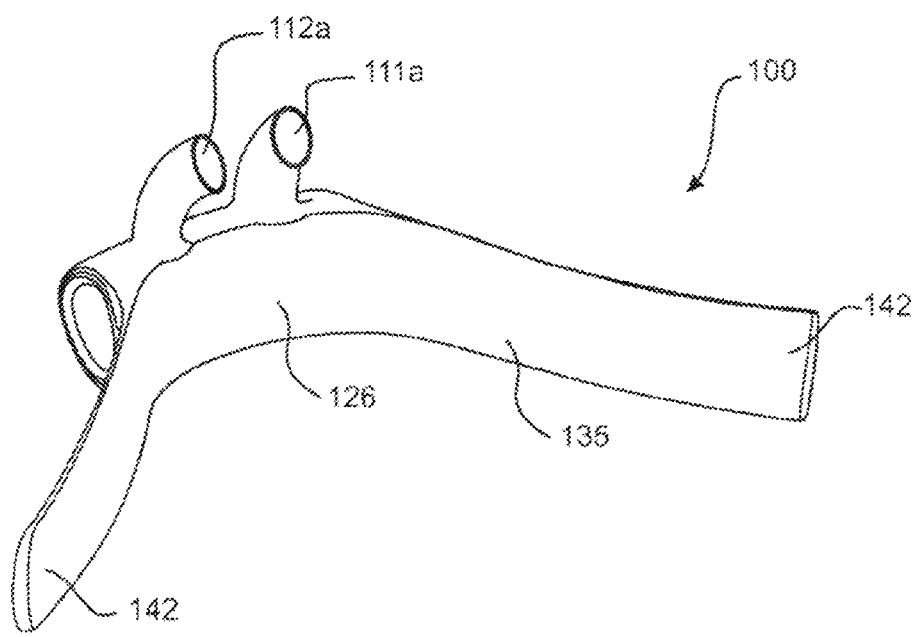
FIG. 3 is a perspective view of the cannula of FIG. 2 viewed from an inner side of the cannula.

In some embodiments the side arms 145a, 145b comprise the side members of the frame and a resilient material 135 over moulded or otherwise covering the side members 147a, 147b of the frame. For example, as illustrated in FIGS. 2 and 3, in some embodiments the frame 140 is over moulded or otherwise covered with a resilient material 135 along each side arm 145a, 145b. Each side arm 145a, 145b thus comprises a relatively rigid member 147a, 147b covered by a relatively resilient material 135. In some embodiments, the nasal prongs may be integrally formed with the resilient material covering the side members 147a, 147b of the frame. As described above, example resilient materials are Silicone, thermoplastic elastomer (TPE), and/or thermoplastic polyurethane (TPU), and example relatively rigid materials such as polycarbonate, high-density polyethylene, low density polyethylene, polypropylene, poly-vinyl chloride, ethylene-vinyl acetate (EVA). In use, the side members 147a, 147b of the frame are formed from a material and are of a suitable geometry or shape so that the side arms of the cannula initially elastically deflect to conform to a profile of a user's face, and then deform by mechanical creep deformation over time during use. The resilient covering of the side arms contacts the user's face in use.

Preferably the frame extends continuously along each side arm from one side of the interface to the other. As illustrated in FIGS. 6 and 7, in some embodiments, the frame comprises a cutout portion 125 facing the user's upper lip in use. The resilient material over moulded to the frame covers over the cut out portion to form a wall of the manifold. The resilient wall provides a resilient pillow 126 (FIG. 3) for contact with the user's upper lip. The manifold comprises the resilient wall.

In some embodiments, each side arm is shaped so that in the un-deflected configuration and with the manifold positioned at or adjacent a user's upper lip, an intermediate section 143 of each side arm 145a, 145b contacts the user's face. For example, with reference to FIG. 8, each side arm may be outwardly curved so that in the un-deflected configuration intermediate section 143 of each side arm contacts the user's face. In some embodiments, in the un-deflected configuration and with the manifold positioned at or adjacent a user's upper lip for use, the intermediate section 143 of each side arm 145a, 145b contacts the user's face in one or more of the lower outer maxilla zone, the upper outer maxilla zone, the zygomatic arch, the maxilla recess, and the central maxilla. Preferably the intermediate section contacts any one or more of the lower outer maxilla, the zygomatic arch and the maxilla recess.

Figure 10:
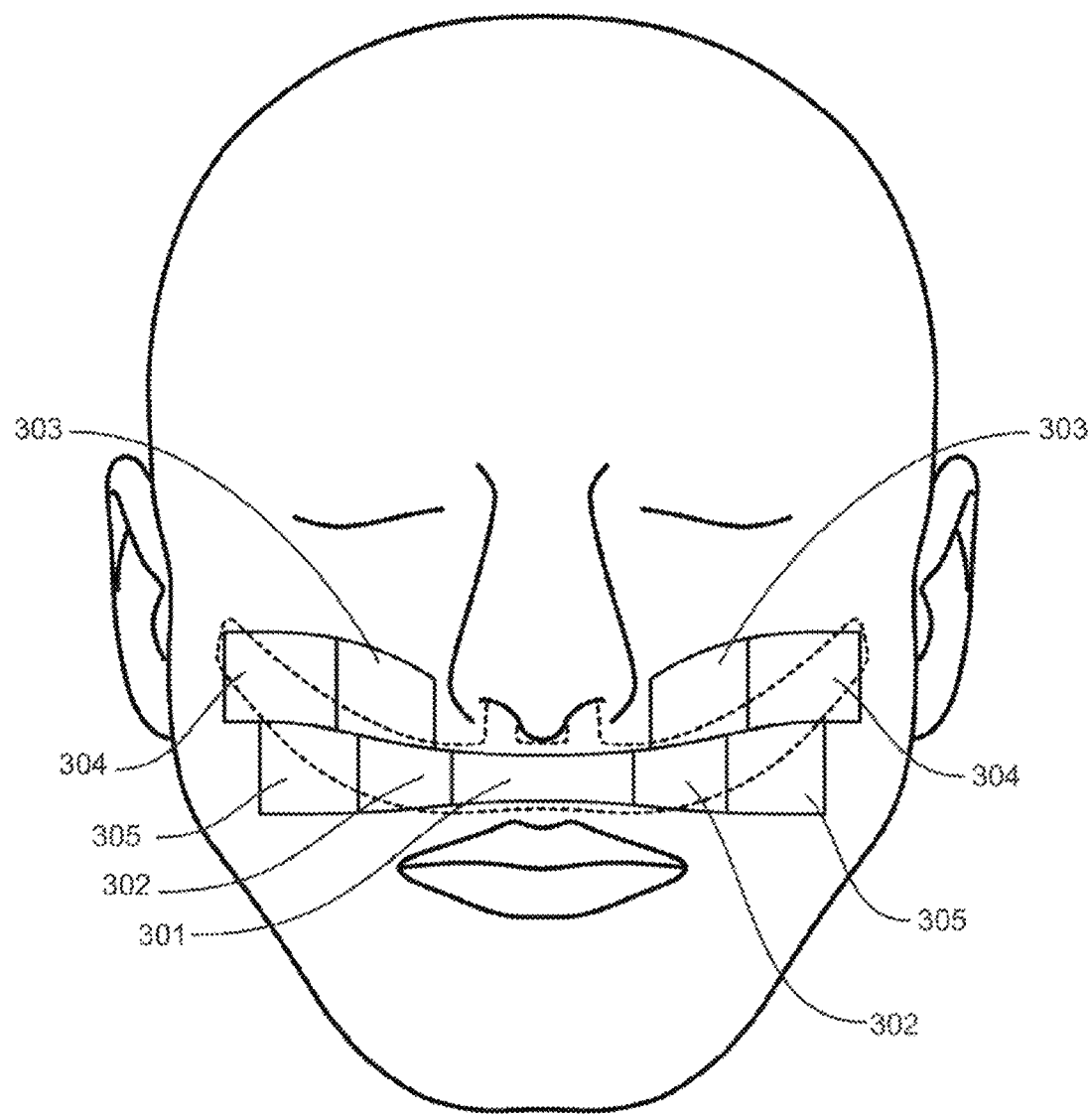
FIG. 10 is a facial map of a user's face identifying zones on a user's face.

Various positions on a user's face are illustrated in FIG. 10. Zone 301 is the central maxilla, zone 302 is the lower outer maxilla zone, zone 303 is the upper outer maxilla zone, zone 304 is the zygomatic arch, and zone 305 is the maxilla recess.

When force is initially applied to the side arms by headgear to deflect the side arms elastically to a deflected state or configuration, the side arms bend at the intermediate section 143 in contact with the user's face to conform to the profile of the user's face. Load or stress may be therefore concentrated in the intermediate section where the bending occurs. The stress is less than the yield stress of the relatively rigid material of the side arms, but the material deforms permanently by mechanical creep deformation so that the side arms conform to the profile of the user's face. In some embodiments, the bending of the side arms at the intermediate section 143 of each side arm causes the manifold or a centre section of the interface to lift away from the upper lip (the central maxilla zone 301) of the user. In such embodiments, the manifold or centre part of the interface may remain spaced from the user's upper lip in use.

While the upper lip may provide a good datum for positioning of a nasal cannula for proper location of the prongs in the nares of a user, a force applied by the cannula against the upper lip is not desirable. By lifting the manifold away from the upper lip in use, force against the upper lip is reduced or avoided to improve comfort during prolonged use of the cannula. Preferably, in a final deformed state the cannula will contact the user's face evenly along the length of both arms, with contact between the user's upper lip and the centre or manifold portion of the cannula avoided.

In the un-deflected state shown in FIG. 8 the cannula is initially wider than the contours of the user's face. In some embodiments, the cannula may be initially narrower than the user's face.

Figure 11A:
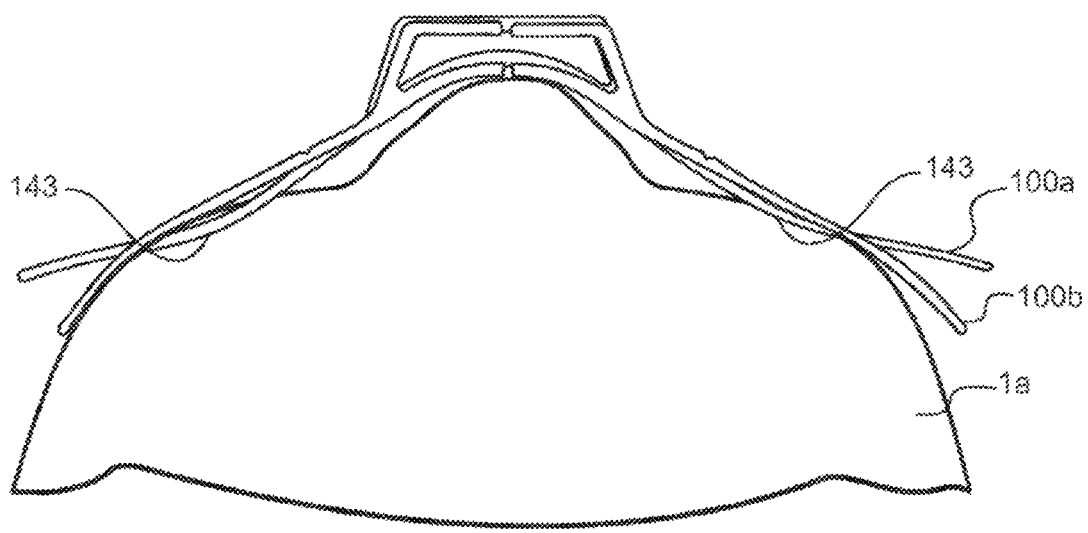
FIG. 11A illustrates result from a test of a cannula that is initially wider than a user's face.
Figure 11B:
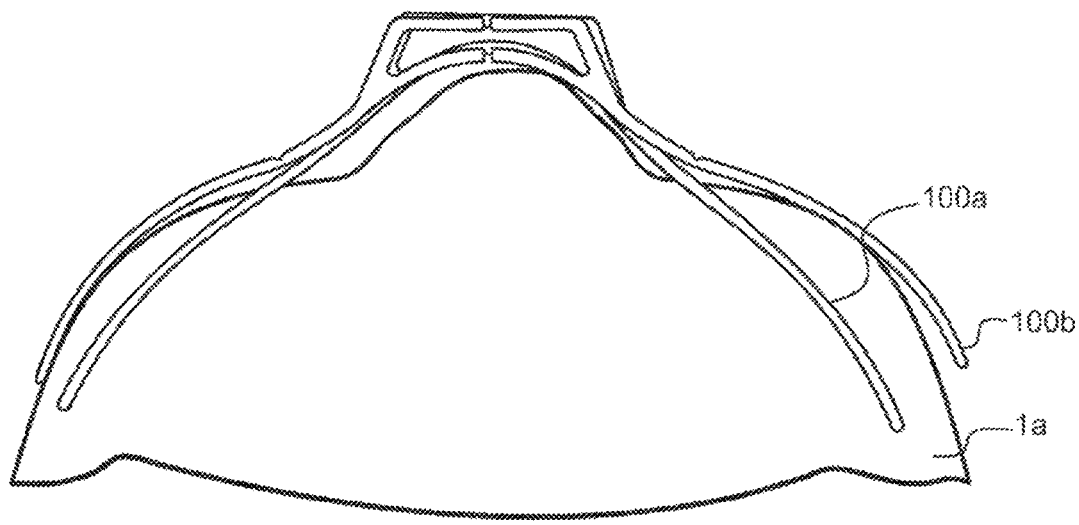
FIG. 11B illustrates result from a test of a cannula that is initially narrower than a user's face.

FIG. 11 shows the result from a test of a cannula that is initially wider than a user's face. The initial shape of the cannula is illustrated as 100a. In the test the cannula is fitted to a Perspex facial contour 1a. In the initial shape the cannula initially makes contact with the facial contour at an intermediate position 143 along each arm 145a, 145b of the cannula. A headgear strap attached to each arm (not shown) applied a typical headgear force to simulate attachment to a user's face simulated by the Perspex facial contour over a 24 hour period. The headgear deflected the cannula to conform to the facial contour. The test was performed at an ambient temperature of 60° C. to accelerate the rate of mechanical creep deformation over the 24 hour period. Once the headgear was released after the 24 hour test period the cannula had conformed to the profile of facial contour by mechanical creep deformation, to hold the shape illustrated as 100b.

FIG. 12 shows the result from a test of a cannula that is initially narrower than a user's face. The cannula is fitted to the Perspex facial contour 1a. The facial contour initially spreads and holds the side arms 145a, 145b apart, and the position of the cannula is maintained on the facial contour by headgear. Initial contact pressure is higher towards the ends of the side arms 145a, 145b. Again the cannula was applied to the facial contour for a period of 24 hours at an ambient temperature of 60° C. to accelerate the rate of mechanical creep deformation over the test period. Once the headgear was released after the 24 hour test period the cannula had conformed to the profile of facial contour by mechanical creep deformation, to hold the shape illustrated as 100b.

Both embodiments of an interface initially being wider than a user's face (wide interface) or narrower than a user's face (narrow interface) may be utilised to fit a wide range of face shapes. A wide interface can be designed to deform by mechanical creep deformation to creep inwards during use to match a user's face. And a narrow interface can be designed to deform by mechanical creep deformation to creep outwards during use to match a user's face. In some embodiments, initial sizing of an undeformed interface may be targeted to either the widest or the narrowest face contour intended for the interface to be used with. For example, in a wide interface embodiment, the undeformed interface fits a user with a wide face. To fit a user with a narrow face the wide interface deforms inwards overtime by mechanical creep deformation.

An interface that is initially too wide for a particular user's face may be more comfortable than an interface that is initially too narrow. A wider interface may be more comfortable to fit to a user's face because being wider the interface tends to apply less stress on the face (than a narrow interface) as the headgear strap applies a force to the interface to match the interface to the contours of the user's face. For an interface that is narrower than a user's face the arms of the interface apply force to the user's face to deflect and match the contours of the user's face and which may be less comfortable. However, mechanical creep deformation of a narrow interface to fit a wider facial contour may be more successful at forming a good fit to a patient's face as the interface may have more contact with the patients face as it changes shape.

Ideally, a patient interface will have no or minimum contact with the central maxilla zone of the patient. Preferably, in both an un-deflected or undeformed configuration and a deformed configuration following mechanical creep deformation, the patient interface will have no or minimal contact with the central maxilla. Preferably, in the final deformed shape following mechanical creep deformation, the interface will contact the face evenly along the length of the side arms 145a, 145b, with no or minimal contact between the interface and central maxilla zone.

For a wide interface (interface that is wider than a user's face prior to mechanical creep deformation) initial contact pressure is predominantly in the upper or lower outer maxilla zones. Following mechanical creep deformation of a wide interface, contact is pressure between the interface and the user's face is more evenly spread over the upper or lower outer maxilla zones and the zygomatic arch or maxilla recess zones.

For a narrow interface (interface that is narrower than a user's face prior to mechanical creep deformation) initial contact pressure is predominantly in the zygomatic arch or maxilla recess zones. Following mechanical creep deformation of a narrow interface, contact is pressure between the interface and the user's face is more evenly spread over the upper or lower outer maxilla zones and the zygomatic arch or maxilla recess zones.

In some embodiments the interface allows for the side arms of the interface to deform laterally with respect to a user's face. For example, with reference to FIGS. 18A and 18B, in some embodiments the side arms of the interface deform by mechanical creep deformation to orientate the arms to be in line with a headgear strap attached to the side arms. FIG. 18A shows the arms prior to mechanical creep deformation and FIG. 18B shows the arms after mechanical creep deformation.

In some embodiments the interface comprises 'creep zones' that are localised sections or areas of the patient interface in which mechanical creep deformation is confined or predominant in the interface. An area that that is difficult to fit to a range of user's faces (due to large variation between different users) may be configured to be more prone to mechanical creep deformation than other areas.

In some embodiments, a creep zone may be formed from a material that is different to the material of other parts of the interface. A zone of different material to form a creep zone may be achieved by having a material forming process in the creep zone that is different to a material forming process in other areas of the interface. For example, during a moulding process in which an interface is made, plasticisers may be added to a localised area of the interface to form a creep zone. Alternatives may be the addition of a filler material or materials in a creep zone, or the creation of mechanical stress in the creep zone by, for example, designing a mould tool to achieve or promote a particular material flow in the creep zone during moulding.

A creep zone may be formed after a moulding process is completed. For example, an area of a patient interface may be heat treated post moulding, or an interface may be made from a UV sensitive material, and a creep zone may be created by applying UV light to the zone.

Figure 12A:
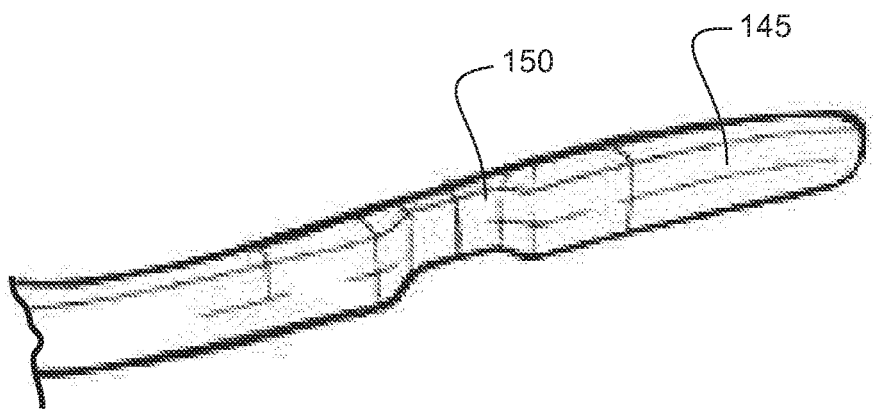
FIGS. 12A to 12C illustrate a part of a side arm of a patient interface with a creep zone formed by a reduced cross section.
Figure 12B:
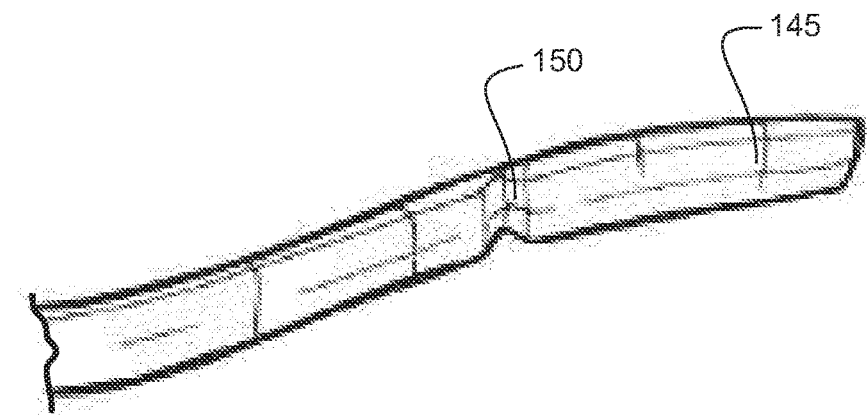
Figure 12C:
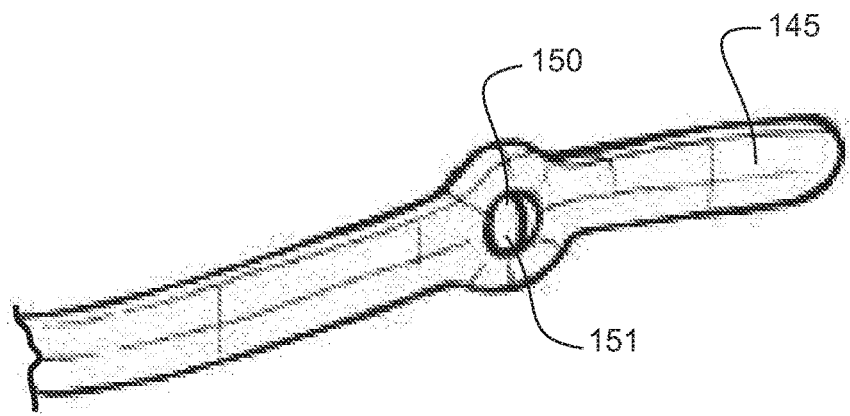

A creep zone may be created by a locally different cross section. For example, in some embodiments a creep zone may comprise a reduced cross section compared to other areas of the interface. In some embodiments the creep zone may be formed as a thinner or narrower section in the interface. For example, as illustrated in FIGS. 12A and 12B, a creep zone 150 is formed by a reduced thickness section in a side arm 145 of an interface (partly shown) that preferentially deforms by mechanical creep deformation compared to sections of the side arm on either side of the creep zone 150. The cross section in a creep zone may be reduced by a cut-out in the zone, for example cut-out 151 as shown in FIG. 12C.

Further examples of creep zones in a side arm of an interface are provided in FIGS. 13A to 13E. In these examples the thickness of the creep zone 150 may be the same or similar to the thickness of the arm in other areas, however, the cross section in the creep zone is reduced by having a narrower section (FIG. 13E) or by having a cut-out portion or portions 151.

The creep zone geometries illustrated in FIGS. 13A to 13E were tested by applying a weight to an end of each illustrated specimen. The weight was chosen to simulate a typical patient interface headgear strap tension. The weight was applied over a 24 hour time period, and then an extension of the creep zone was recorded. The results (length extension in mm) are presented in the table below. The cross sectional area for each creep zone was the same, being 4 mm2.

|  | Circle (FIG. 13A) | Diamond (FIG. 13B) | Square (FIG. 13C) | Parallel slots (FIG. 13D) | Neck (FIG. 13E) |
| --- | --- | --- | --- | --- | --- |
| Cross sectional area | 4 mm$^2$ | 4 mm$^2$ | 4 mm$^2$ | 2 mm$^2$ | 2 mm$^2$ |
| Test 1 | 7.16 mm | 8.18 mm | 9.61 mm | 14.02 mm | 13.53 mm |
| Test 2 | 10.14 mm | 11.23 mm | 9.05 mm | 15.03 mm | 13.24 mm |
| Test 3 | 11.65 mm | 10.38 mm | 10.87 mm | 13.66 mm | 16.43 mm |

The results show that there is a greater extension for a creep zone with a reduced cross section. The extension for the parallel slots and necked zones was greater than the extension of the other creep zones with a larger cross sectional area. The majority of the extension of the specimens was elastic deformation that occurred upon initial loading. Each specimen then deformed by mechanical creep deformation, to maintain the final elongated shape even after loading was removed.

A number of creep zones may be utilised in a patient interface to promote creep in defined positions to achieve a fitted interface. A number of areas identified as being useful locations to include creep zones are described with reference to FIG. 14. FIG. 14 illustrates a nasal cannula, from below or above (nasal prongs not shown). In some embodiments, the side arms may each comprise more than one creep zone, two said creep zones spaced apart by a non-creep zone or stable zone. A non-creep or stable zone or a dimensionally stable area is a zone or area of the interface that does not plastically deform during normal use of the interface. For example, in some embodiments the manifold or central portion of a cannula is dimensionally stable and therefore does not deform during use. As discussed above, preferably the cannula will maintain minimal or no contact under the nose of the user. The geometry of the manifold or central portion may be designed to fit a majority of the population of users. Deformation or deflection in the manifold or central portion may cause the manifold or central portion to widen which would act to bring the cannula closer to the users face under the nose. Therefore in some embodiments deformation or deflection of the manifold or central portion is resisted by making this portion of the cannula dimensionally stable under normal conditions of use. Further, dimensional stability of the manifold may be desirable to maintain functionality between mating components. For example, in some embodiments a breathing tube may be releaseably fitted to the manifold part. To ensure correct connection between the manifold and tube the manifold, in some embodiments the manifold is dimensionally stable so that the tube correctly fits with the manifold (for example without breathing gas leakage).

In some embodiments, each side arm has a creep zone at an intermediate position along the arm, in between two dimensionally stable zones. For example, with reference to FIG. 14, in some embodiments a cannula may have a side arm with a first dimensionally stable portion 161 at an inner end of the arm, a second dimensionally stable portion 162 or 163, and a creep zone 150a in between the first and second dimensionally stable portions. The second dimensionally stable portion 162 may be at an outer end of the arm, or may be located part way along the arm.

In some embodiments, each side arm has two creep zones 150a and 150b. In some embodiments, each arm comprises a first dimensionally stable zone 161 at an inner end of the arm and a second dimensionally stable zone 162 partway along the arm, a first creep zone 150a in between the first and second dimensionally stable zones, and a second creep zone 150b outside the second dimensionally stable zone 162, towards or at an outer end of the arm. One of the creep zones is an inner creep zone 150a, being nearer to a central part of the interface, and the other creep zone is an outer creep zone 150b, being nearer to an outer end of the arm.

As illustrated in FIG. 14, in some embodiments each side arm comprises a dimensionally stable zone 161, 163 at each end of the arm, a third dimensionally stable zone 162 part way along the arm, and two creep zones 150a, 150b, each creep zone located between an end of the arm and the third dimensionally stable zone 162. In some embodiments, the arm has two dimensionally stable zones 161 and 162, and two creep zones 150a, 150b, wherein the outer creep zone extends to the outer end of the arm.

Small deflections of the arms at inner ends of the arms can cause large positional changes at the outer ends of the arms. Mechanical creep deformation at an inner creep zone 150a controls how wide or narrow an overall shape of the interface is.

A dimensionally stable zone 162 part way along the arm may be useful in that a detail such as a tubing clip may be provided to the arm that is not affected by creep deformation. A clip detail provided at zone 162 formed from a stable material will maintain dimensional tolerances so that functionality of the clip is maintained.

An outer creep zone 150b may allow an interface that is too broad or wide and flat for a patient to wrap around the user's face.

Having spaced apart creep zones allows for an arm that can deform in separate defined locations which may assist to conform the arms of the interface to a user's face by mechanical creep deformation. Both inner and outer creep zones may be encouraged to creep to achieve changes to better suit a user's face.

In preferred embodiments the manifold or central area of a cannula is dimensionally stable. Therefore, in some embodiments the inner end of the arm is also dimensionally stable. In some embodiments, as illustrated in FIG. 14, an outer end portion 163 of the cannula arm is also dimensionally stable to maintain dimensional tolerances so that functionality of a connection detail (for example a buckle) for connecting with headgear is maintained.

As described above, in some embodiments a patent interface may be shaped to match a user's face by mechanical creep deformation during use. However, in some embodiments the interface may be additionally or alternatively shaped by mechanical creep deformation post manufacture and prior to use. In some embodiments, the patient interface is shaped by mechanical creep deformation by holding the interfaced in a particular shape by a brace. A brace may be incorporated into or form part of packaging. When the interface is to be used the packaging is removed from the interface and may be discarded or recycled. In some embodiments the packaging forms a brace or jig. For example, packaging may provide an open box or brace or bracketing for holding the interface in a particular shape. The packaging deflects the interface from an un-deflected configuration to a deflected configuration. The interface is adapted to deform by mechanical creep deformation so that after the interface has been held by the packaging in the deflected configuration for a time period the interface is permanently formed into a formed configuration. The packaging may form the interface from a basic shape into a more complex shape by mechanical creep deformation by holding the interface in a deflected configuration.

Interfaces are typically manufactured by injection moulding. Features on the interface such as tubing clip details or head gear strap buckles or clips are typically designed to take into account practicalities of the moulding process. Designing features to be suitable for moulding becomes more complex and difficult as the interface becomes more complex. For example, a desired shape of a cannula may comprise a changing angle of twist along the side arms of the cannula. Requirements for mould design can lead to distortions of proportions and dimensions of details on the side arm to allow for moulding considerations such as a flow of material into mould cavities, ejection of the part from the cavity and parting lines. A more simplified shape of cannula for example a cannula without twist in the side arms can be easier to mould and can make the design of details such as clips on the side arms easier to design with the moulding process in mind.

Thus, an interface that is adapted for mechanical creep deformation and a brace for holding the interface in a deflected position to achieve a formed configuration post moulding can allow for simpler moulding tool design and avoid a compromise in the design of detailed features of the interface resulting from moulding process considerations.

Furthermore, an interface that is adapted for mechanical creep deformation and a brace for holding the interface in a deflected position to achieve a formed configuration post moulding can allow for a single moulded shape to be formed into many different formed shapes for use by a broad range of users. For example, a single basic interface shape may be formed by mechanical creep deformation by a brace into a range of different formed shapes, for example a small interface shape, medium interface shape, and a large interface shape. A range of basic interface shapes may be provided. For example, a small, medium and large interface may be moulded. A range of braces may be used to create a range of formed configurations for each of the small, medium and large basic interface shapes. For example, for each of the small, medium and large interfaces, a range of narrow to wide interface shapes may be created by mechanical creep deformation caused by a range of braces holding the basic interface in one of a number of possible a deflected configuration. Further, the amount of curvature and/or angle of twist in side arms of the interface may be achieved by mechanical creep deformation caused by a brace holding the interface in a deflected configuration. Thus complex shapes can be formed when the interface is stored in packaging to allow for moulding of simplified interface shapes. A range of different shapes can be provided without the need for different moulding tools, and custom sizing or shapes can be achieved from a single or reduced number of base moulded shapes.

In some embodiments, an interface that is adapted to deform by mechanical creep deformation is provided with a packaging, wherein the packaging is adapted to hold the interface in a deflected configuration to permanently deform the interface by mechanical creep deformation into a formed configuration. For example the packaging comprises a brace as described above.

Figure 15:
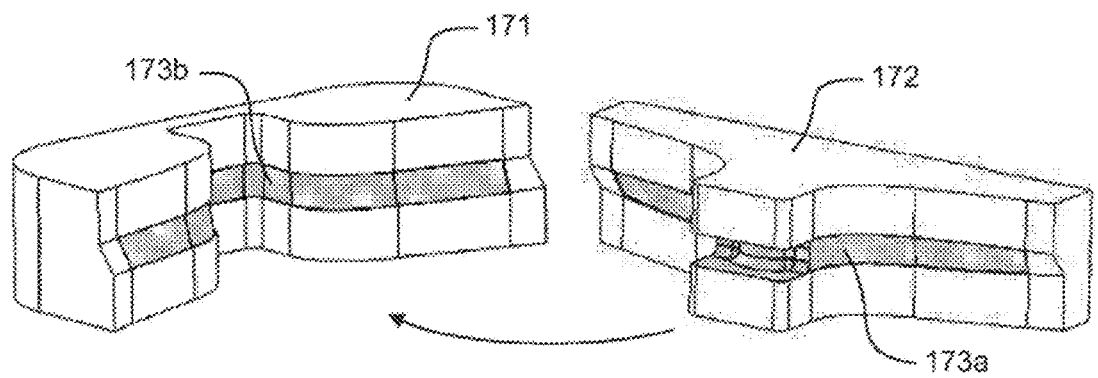
FIG. 15 illustrates a brace for holding a patient interface in a deflected configuration.

With reference to FIG. 15, in some embodiments the brace 170 comprises two complementary parts 171, 172 that fit together to form a cavity for receiving and holding the interface in a deflected configuration. The complementary parts 171, 172 may each comprise a part 173a, 173b of the cavity that is formed by the two parts being fitted together. Once released from the cavity provided by the brace the interface retains a formed shape for use by a user. During use, the interface may further deform by mechanical creep deformation described above to fit a particular user's face.

In some embodiments the brace may comprise an open recess or cavity into which the interface is inserted. The interface is inserted into the recess or cavity by deflecting the interface from an un-deflected position to a deflected position. Once the interface is received in the recess or cavity the recess or cavity holds the interface in the deflected position so that the interface achieves a formed configuration over time by creep deformation.

Figure 16:
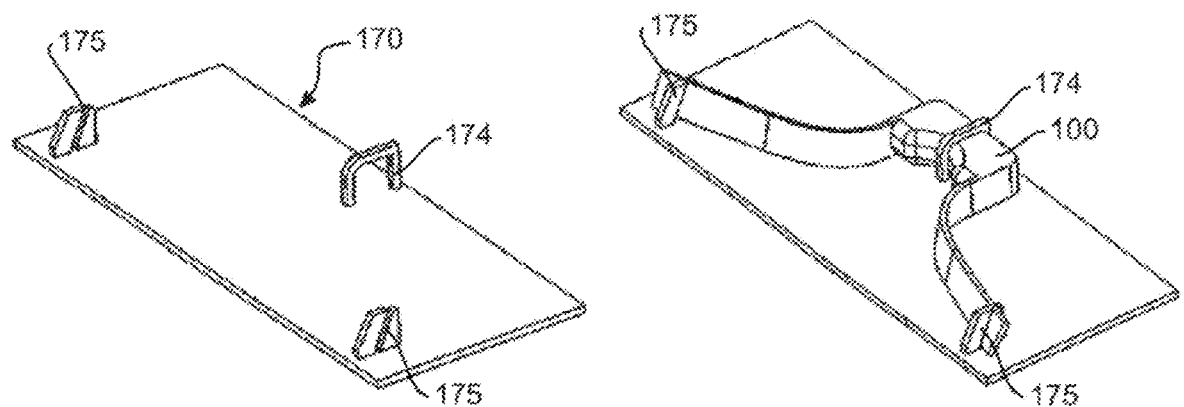
FIG. 16 illustrates another brace for holding a patient interface in a deflected configuration.

In some embodiments the brace may comprise retention details to hold the interface in the deflected configuration. For example, as illustrated in FIG. 16, the brace may comprise a bracket 174 (a support) for holding the central portion or manifold of the cannula, and a bracket 175 for holding each of the cannula side arms in a defected position. The brackets are located on a base of the brace as shown and held in relative positions on the base. In the illustrated embodiment the brackets 175 each comprise a slot that receives a side arm of the interface to hold the arm in a deflected position. In some embodiments the brackets 174, 175 may be posts that are positioned relatively on a base of the brace so that the interface is fitted onto the base in between spaced apart posts to hold the interface in the deflected configuration. The interface is deflected to fit into the brace and contact the brackets which hold the interface in the deflected position. The brace 170 is a holder for holding the interface in a deflected position, and may form part of packaging for wrapping the interface.

Figure 17:
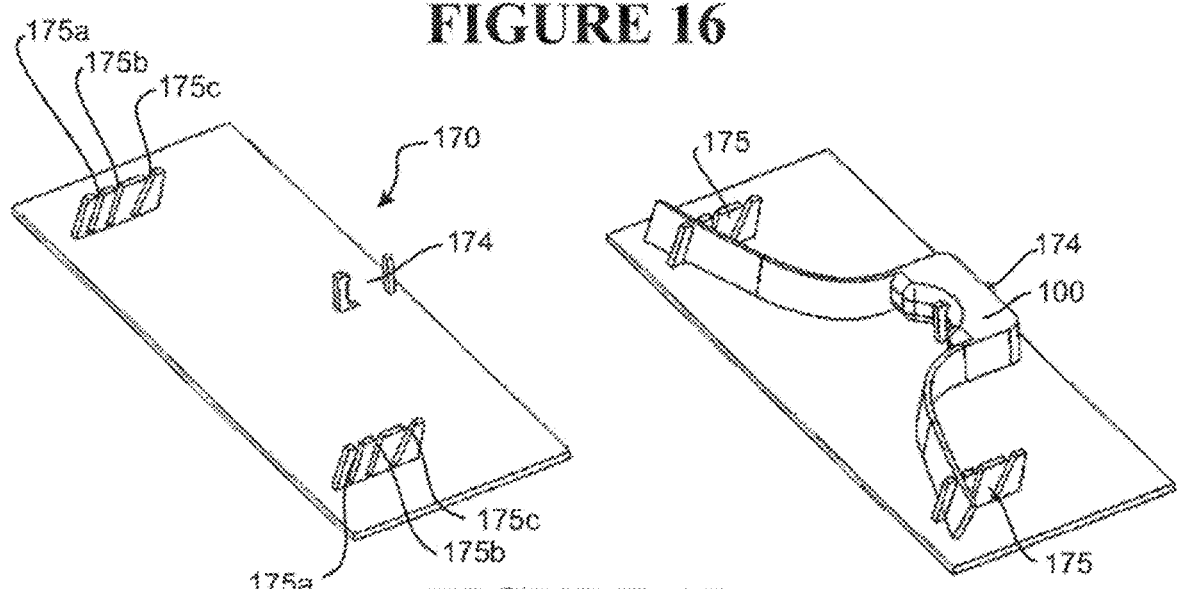
FIG. 17 illustrates another brace for holding a patient interface in a deflected configuration.

In some embodiments, the brace 170 may comprise a set of retention details or brackets corresponding to a number of different formed configurations. The interface may be inserted into the brace or holder in one of a range of available bracket positions to achieve one of a number of possible formed configurations. As shown in FIG. 17, in some embodiments, brackets 175 for holding the arms of a cannula each comprise a number of bracket or brace positions 175a, 175b and 175c to correspond with different formed configurations each having a different width.

Mechanical creep deformation may occur after packaging, while the interface is in warehouse storage and/or when in transit to a retailer or end user. In some embodiments the creep deformation to achieve a formed configuration may occur prior to packaging. For example, prior to packaging an interface adapted for mechanical creep deformation may be fitted into a brace 170. Once a formed configuration is achieved, the interface is removed from the brace and packaged for protection during storage and delivery to an end user.

Creep deformation may be accelerated, for example on an assembly line or after an interface has been packaged, by for example applying increased heat and/or humidity.

In some embodiments the side arms permanently deform by mechanical creep deformation over a time period of less than 2 weeks of use. In a more preferred embodiment the side arms permanently deform by mechanical creep deformation over a time period of less than 1 week. In some embodiments the side arms permanently deform by mechanical creep deformation over a time period of less than 6 days, or 5 days, or 4 days, or 3 days, or 2 days or 1 day. For example, in some embodiments the side arms permanently deform by mechanical creep deformation over a time period of less than 12 hours, or in about 2 hours of use.

In some embodiments the side arms permanently deform by mechanical creep deformation at a temperature that the side arms reach during use with the cannula fitted to a user's face. Heating or warming up of the arms during use through contact with the user's face may be described as passive heating of the arms. For example, during use when in contact with or near to the user's face the user's skin may reach a temperature of about 28° C. to 37° C. at which temperature the side arms 145a, 145b in contact with the skin may further encourage deformation by mechanical creep deformation. In some embodiments the side arms deform by mechanical creep deformation at or around room temperature, for example at 18oC to 30oC. In some embodiments the side arms may deform by mechanical creep deformation at a temperature of about 18° C. to 37° C., or 28° C. to 37° C., or 18° C. to 35° C., or 18° C. to 30° C., or 30° C. to 35° C.

In some embodiments the side arms of the interface may be heated (active heating) to promote mechanical creep deformation. For example, in some embodiments, each side arm comprises a heater element such as a heater wire. An electrical current passing through the heater wire causes the wire to dissipate heat into the material forming the side arms to raise the temperature of the material and accelerate mechanical creep deformation. In some embodiments, the temperature of the arms may be increased by directing a flow of heating respiratory gases to be delivered to the patient's airway along the arms. The temperature of the gases may raise the temperature of the arms to promote mechanical creep deformation. In some embodiments a heater wire for heating the flow of respiratory gases to the users nares may be also used to heat the side arms to promote mechanical creep deformation.

In some embodiments the arms of the interface may include material or a heat pack comprising chemicals that can be user-activated to cause a chemical reaction to produce heat. The chemical reaction produces heat to heat the material of the arms of the interface to promote mechanical creep deformation. In some embodiments the arms of the interface may be formed from a material that is adapted to be heated by submersing in warm water. In some embodiment the interface may be adapted to deform by mechanical creep deformation at temperatures reached during processing in an autoclave, for example for sterilisation. A typical autoclave temperature might be in the range of about 100 to 140° C.

In some embodiments the patient interface is adapted to deform by mechanical creep deformation at a temperature in the range of about 20° C. to about 150° C., or about 30° C. to about 140° C., or about 40° C. to about 130° C., or about 50° C. to about 120° C.

By way of example interfaces have been described above with side arms of the interface that are adapted to deform by mechanical creep deformation. However, other areas of an interface may deform by mechanical creep deformation. For example, in some embodiments a cannula may comprise nasal prongs that are adapted to deform by mechanical creep deformation. As shown in FIG. 19, the dashed lines indicate an un-deflected position of nasal prongs, for example prior to use. During use, contact between the prongs and the nares of the user (for example as indicated by the arrow in FIG. 19) may cause the prongs to be forced to a deflected configuration. Over a period of time, due to mechanical creep deformation, the prongs are permanently deformed to a formed configuration, for example as shown by the continuous lines in FIG. 19.

The side arms deform under the force applied by the headgear in use. For example, in order to retain the patient interface in position on the user's face the headgear may pull the interface against a users face at a force in the range of about 0.1N to 5N. In some embodiments the headgear provides a force of about 0.1N to 1.5N, or about 0.1N to 1.0N, or about 0.2N to 0.5N, or about 0.2N to 0.4N, or about 0.2N to 0.3N, or about 0.3N to 0.5N, or about 0.3N to 0.4N or about 0.4N to 0.5N, or about 0.1N or about 0.2N, or about 0.3N, or about 0.4N, or about 0.5N.

In some embodiments only the side arms of the patient interface deform in use by mechanical creep deformation. For example, the manifold or central portion 120 of the cannula from which the side arms extend does not deform during use by mechanical creep deformation. The material thickness of the manifold part 120 of the frame may be sufficient to prevent permanent deformation of the manifold part of the frame during use. As shown in FIG. 7, in some embodiments the frame may comprise a bracketing or support feature 146 between the side arm and the manifold 120 so that bending or other deforming stresses are isolated to the side arms. In use stress in the central part 120 of the patient interface does not reach levels sufficient to cause deformation by mechanical creep deformation.

In some embodiments the geometry of the side arms is configured to achieve a desired amount of permanent deformation through mechanical creep deformation. For example, the cross sectional area and/or shape of the side arms or the side members of the frame forming or extending along the side arms is chosen to achieve a desired amount of permanent deformation by mechanical creep deformation. The thickness of the side arm or side member of the frame may be varied along the length of the side arm. For example, in an embodiment where the arms are shaped so that an intermediate portion of the arms contacts the user's face when in the un-deflected state, the sectional thickness of the relatively rigid material of the side arms at the intermediate portion may be thinner than in other positions along the arm so that deformation by mechanical creep deformation occurs preferentially at the intermediate portion of the side arm. Specific examples of localised creep zone configurations are provided above.

The foregoing description of the invention includes preferred forms thereof. Modifications may be made thereto without departing from the scope of the invention as defined by the accompanying claims.

The invention claimed is:

1. A system comprising:
a patient interface comprising one or more creep zones, an un-deflected configuration, a deflected configuration and a formed configuration,
wherein the one or more creep zones are adapted to elastically deflect, under the application of a force, from the un-deflected configuration to the deflected configuration, and to permanently deform when in the deflected configuration for a period of time by mechanical creep deformation to the formed configuration; and
a brace configured to receive the patient interface in the un-deflected configuration and to hold the patient interface in the deflected configuration, wherein the patient interface is configured to be in the formed configuration when the brace holds the patient interface in the deflected configuration for the period of time.

2. The system as claimed in claim 1, wherein the interface comprises:
a manifold adapted to receive a flow of gases, and
a side arm extending from each side of the manifold, each side arm comprising at least one of the one or more creep zones.

3. The system as claimed in claim 2, wherein each side arm is outwardly curved or shaped so that in an un-deflected configuration and with the manifold positioned at or adjacent a user's upper lip for use, an intermediate section of each side arm contacts the user's face.

4. The system as claimed in claim 2, wherein each side arm comprises a heater wire.

5. The system as claimed in claim 1, wherein the interface comprises a manifold adapted to receive a flow of gases and one or two nasal prongs extending from the manifold, wherein each nasal prong comprises at least one of the one or more creep zones.

6. The system as claimed in claim 1, wherein in the formed configuration the interface conforms with the profile of the user's face without application of a force or under a force that is reduced compared to the force applied to elastically deflect the interface from the un-deflected configuration to the deflected configuration.

7. The system as claimed in claim 1, wherein each of the one or more creep zones is formed from a material that is different to the material of other parts of the interface and, wherein each of the one or more creep zones is formed by a material forming process that is different to a material forming process in other areas of the interface.

8. The system as claimed in claim 1, wherein each of the one or more creep zones has a reduced cross section compared to areas of the interface adjacent to each of the one or more creep zones.

9. The system as claimed in claim 8, wherein each of the one or more creep zones comprises a section with a cut-out.

10. The system as claimed in claim 9, wherein each of the one or more creep zones comprises more than one cut-out.

11. The system as claimed in claim 9, wherein each of the one or more creep zones comprises a thinner or narrower section in the interface.

12. The system as claimed in claim 1, comprising a manifold adapted to receive a flow of gases, and a side arm extending from each side of the manifold, and wherein each side arm comprises at least one of the one or more creep zones and one or more dimensionally stable zones.

13. The system as claimed in claim 12, wherein the side arms each comprise at least two of the one or more creep zones spaced apart by a dimensionally stable zone of the one or more dimensionally stable zones.

14. The system as claimed in claim 13, wherein the one or more dimensionally stable zones comprises a first dimensionally stable zone and a second dimensionally stable zone, wherein the one or more creep zones comprises a first creep zone and a second creep zone, and wherein each side arm comprises the first dimensionally stable zone at an inner end of the side arm and the second dimensionally stable zone partway along the side arm, the first creep zone in between the first and second dimensionally stable zones, and the second creep zone outside the second dimensionally stable zone towards or at an outer end of the side arm.

15. The system as claimed in claim 14, wherein the one or more dimensionally stable zones further comprises a third dimensionally stable zone and a fourth dimensionally stable zone, wherein the one or more creep zones further comprises a third creep zone and a fourth creep zone, wherein each side arm further comprises the fourth dimensionally stable zone at each end of the side arms, the third dimensionally stable zone part way along the side arm, and the third and fourth creep zones located between each end of the side arms and the third dimensionally stable zone.

16. The system as claimed in claim 12, wherein at least one of the one or more creep zones is located in the side arm to correspond with the lower outer maxilla zone, the upper outer maxilla zone, the zygomatic arch, the maxilla recess, or the central maxilla.

17. The system as claimed in claim 1, wherein at least one of one or more creep zones deform by mechanical creep deformation in areas of high skin contact pressure.

18. The system as claimed in claim 1, wherein a stress in the one or more creep zones causes the one or more creep zones to permanently deform by mechanical creep deformation over the period of time remains below a yield stress of a material of the one or more creep zones.

19. The system as claimed in claim 1, comprising a frame and a resilient material at least partly covering the frame, wherein the frame is adapted to deform by mechanical creep deformation to conform to a profile of a user's face and wherein the frame comprises side members forming side arms of the interface each side arm comprising a said side member of the frame and the resilient material covering the side member of the frame.

20. The system as claimed in claim 19, wherein said side members are formed from a material and are of a suitable geometry such that a combination of one or more of:
  i) the temperature reached by the side members during use when fitted to a user's face, and
  ii) a force applied to the side members by headgear during use when fitted to the user's face, and
  iii) a period of time the patient interface is fitted to the user's face,
  provides for an effective amount of permanent deformation by mechanical creep deformation to occur in the side members for an anatomical fitment of the patient interface to the profile of the user's face.

* * * * *

UNITED STATES PATENT AND TRADEMARK OFFICE
CERTIFICATE OF CORRECTION

PATENT NO. : 10,821,253 B2  
APPLICATION NO. : 15/508837  
DATED : November 3, 2020  
INVENTOR(S) : Laurence Gulliver Page 1 of 1

It is certified that error appears in the above-identified patent and that said Letters Patent is hereby corrected as shown below:

In the Specification

In Column 5, Line 8, delete "face" and insert --face.--.

In Column 7, Lines 57-58, delete "deformation" and insert --deformation.--.

In Column 8, Line 23, delete "manner" and insert --manner.--.

In Column 16, Line 2, delete "that that is" and insert --that is--.

In Column 20, Line 62, delete "18oC to 30oC" and insert --18° C. to 30° C.--.

In Column 21, Line 51, delete "a users" and insert --a user's--.

In the Claims

In Column 24, Line 14, Claim 17, delete "of one" and insert --of the one--.

In Column 24, Line 26, Claim 19, delete "interface" and insert --interface,--.

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*